United States Patent [19]
De Rossi et al.

[11] 4,456,013
[45] Jun. 26, 1984

[54] CATHETER

[75] Inventors: Danilo E. De Rossi, Pisa, Italy; Pierre M. Galletti, Providence, R.I.; Paolo Dario, Leghorn, Italy

[73] Assignee: Brown University Research Foundation, Providence, R.I.

[21] Appl. No.: 299,740

[22] Filed: Sep. 8, 1981

[51] Int. Cl.³ .............................................. A61B 5/02
[52] U.S. Cl. .................................. 128/675; 128/748; 73/727
[58] Field of Search .............................. 128/672–675, 128/748; 73/726, 727

[56] References Cited

U.S. PATENT DOCUMENTS

| | | | |
|---|---|---|---|
| 2,949,910 | 8/1960 | Brown et al. | 73/727 X |
| 3,088,323 | 5/1963 | Welbowitz et al. | 128/675 X |
| 3,406,572 | 10/1968 | Robillard | 73/727 |
| 3,710,781 | 1/1973 | Hutchins et al. | 128/675 |
| 4,191,193 | 3/1980 | Seo | 128/675 |
| 4,274,423 | 6/1981 | Mizuno et al. | 128/675 |

FOREIGN PATENT DOCUMENTS 733638  5/1980  U.S.S.R. .............................. 128/748

Primary Examiner—Lee S. Cohen

[57] ABSTRACT

A catheter including a support suitable for insertion into a body organ, a transducer carried by the support, the transducer including a flexible piezoelectric polymeric membrane, and a pair of surface electrodes mounted on the membrane, the support including a rigid portion defining a flexure cavity inside the catheter, the membrane being mounted on the rigid support portion to permit free flexing of the membrane into and out of the cavity, one surface of the membrane communicating with the cavity, the other surface of the membrane being exposed to the exterior of the catheter to receive and flex in response to pressure variations in the organ, and an electrical cable for transmitting from the electrodes to external circuitry electrical signals produced by said flexure.

15 Claims, 10 Drawing Figures

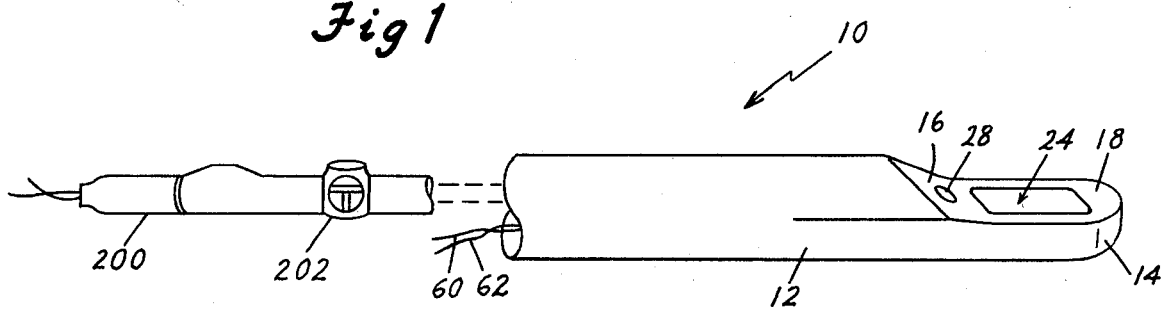
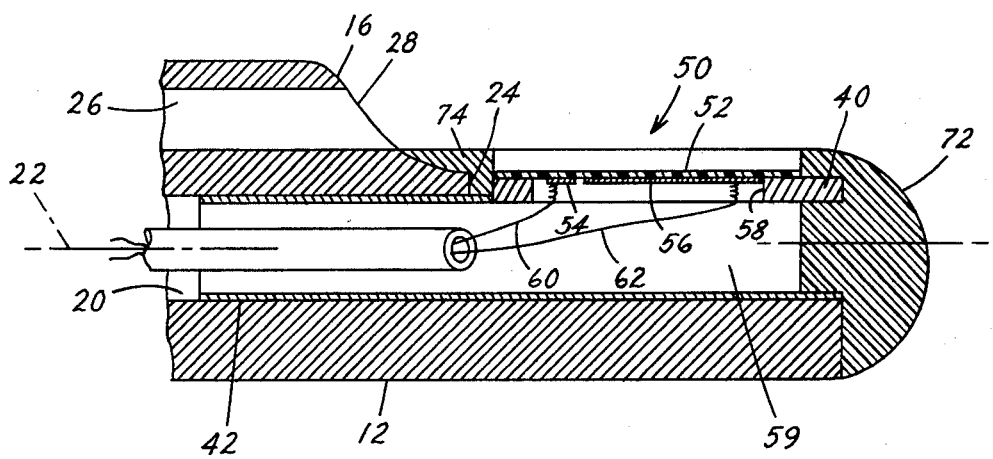

CATHETER

BACKGROUND OF THE INVENTION

This invention relates to catheters useful, e.g., for measuring conditions inside a living body.

Various efforts have been made to measure pressure inside body organs or blood vessels for medical diagnostic and monitoring purposes. The possibility of using piezoelectric polymer material in sensors for this purpose has been suggested, and a catheter using a piezoelectric sensing element is described in U.S. Pat. No. 4,191,193.

SUMMARY OF THE INVENTION

In general the invention features in one aspect a catheter comprising a support suitable for insertion into a body organ, a transducer carried by the support, the transducer comprising a flexible piezoelectric polymeric membrane, and a pair of surface electrodes mounted on the membrane, the support comprising a rigid portion defining a flexure cavity inside the catheter, the membrane being mounted on the rigid support portion to permit free flexing of the membrane into and out of the cavity, one surface of the membrane communicating with the cavity, the other surface of the membrane being exposed to the exterior of the catheter to receive and flex in response to pressure variations in the organ, and means for transmitting from the electrodes to external circuitry electrical signal produced by the flexure.

In preferred embodiments the membrane is poled $PVF_2$; the entire portion of the membrane carrying the electrodes is in registry with the cavity to maximize the ability to flex; and the catheter has a flexible plastic tube with the rigid portion being an insert in the tube and having an opening as part of the cavity and communicating with a lead-carrying lumen in the tube.

In some preferred embodiments the insert has a plate on which the membrane is mounted; and the electrodes are interdigitated on the surface of the membrane facing the cavity. In other preferred embodiments the insert has a transverse opening and a bore extending from a wall of the opening into the catheter, the membrane being mounted in the opening and covering the bore, the bore including the cavity; the membrane is concave; and the electrodes are in a generally circular, interdigitated pattern, both on the surface of the membrane communicating with the bore. In yet other preferred embodiments the catheter has a calibration lumen for receiving fluid at known pressure to calibrate the transducer.

In another aspect the invention features a flexible polymeric tube suitable for insertion into a body organ, a first electrode contacting a limited portion of the outer surface of the tube, a second electrode contacting the inner surface of the tube, the tube being poled to have piezoelectric characteristics over a limited zone including the limited portion of the outer surface, and means for transmitting from the electrodes to external circuitry electrical signals produced by deformation of the zone in response to pressure variations in the organ. In some preferred embodiments the electrodes are concentric rings; in other preferred embodiments the second electrode is conductive fluid filling the tube.

In its various aspects the invention provides a catheter with a high degree of sensitivity, yet easily and inexpensively manufactured, and simple and reliable in operation.

Other advantages and features of the invention are apparent from the description of preferred embodiments thereof.

DESCRIPTION OF THE PREFERRED EMBODIMENTS

The structure and operation of preferred embodiments of the invention will now be described, after first briefly describing the drawings.

DRAWINGS

FIG. 1 is an isometric view of a catheter of this invention.

FIG. 2 is an enlarged sectional view of the tip of the catheter of FIG. 1.

FIG. 3 is an enlarged isometric view of an insert portion of FIG. 2.

STRUCTURE

Figure 4:
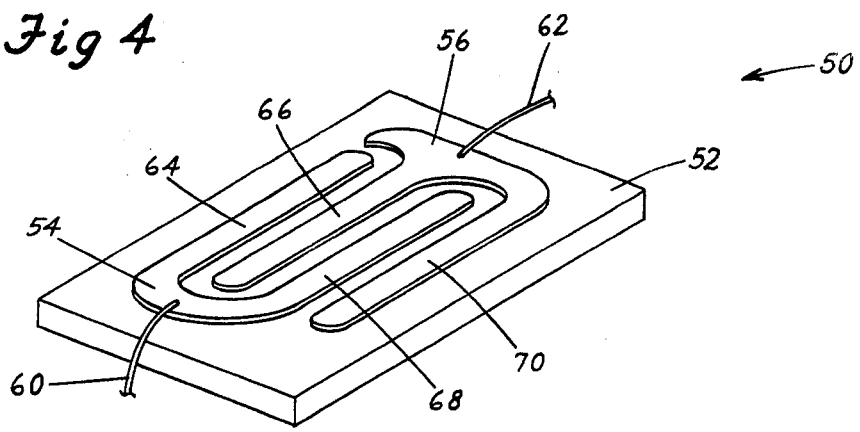
FIG. 4 is an enlarged isometric view of a transducer portion of FIG. 2.
Figure 5:
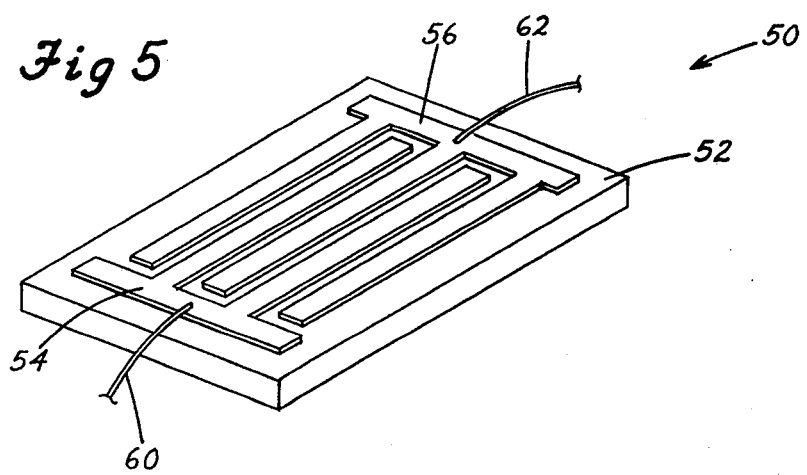
FIG. 5 is a view similar to FIG. 4 showing an alternate transducer.
Figure 6:
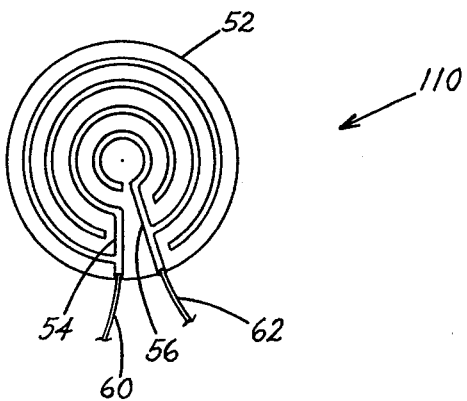
FIG. 6 is a plan view of yet another transducer.

Referring to FIGS. 1-6, catheter 10 has a generally cylindrical soft plastic tube 12 (e.g., of PVC) cut away at its tip 14 to provide a sloping surface 16 and a platform 18. Main lumen 20 extends along the central axis 22 of the catheter and communicates with rectangular opening 24 through platform 18. Lumen 26 is parallel to lumen 20 and opens to the exterior through hole 28 in surface 16.

Rectangular (2×10 mm) stainless steel plate 40 is mounted in opening 24 and fixed to stainless steel tube 42 in lumen 20.

Transducer 50, a thin piezoelectric polymer (preferably poled capacitor grade Solvay polyvinylidene fluoride, "$PVF_2$") film 52 carrying vacuum deposited silver electrodes 54 and 56 on one side, is cemented to plate 40 with the electrodes face down and communicating with lumen 20 through opening 58 in plate 40 and through cavity 59 in tube 42. As shown in FIG. 2, piezoelectric film 52 is supported at its periphery on plate 40 and is unsupported where it overlies opening 58. Leads 60 and 62 connected to the electrodes pass through lumen 20 for connection to external circuitry (not shown).

As shown in FIG. 4, electrodes 54 and 56 have alternating, evenly spaced interlocking fingers 64, 66, 68, and 70 arranged in a generally oval "interdigitated" pattern, and opening 58 is oval to match. Alternatively (FIG. 5), the electrode pattern can be rectangular, or (FIG. 6) even circular; the shape of plate 40 and its opening 58 would vary correspondingly.

The tip of the catheter is potted with epoxy at 72, and epoxy seals plate 40 to tube 12 at 74.

The embodiments of FIGS. 7-10 have elements corresponding to those of FIGS. 1-4, as indicated by the use of common reference numerals; we now describe how these embodiments differ.

Figure 7:
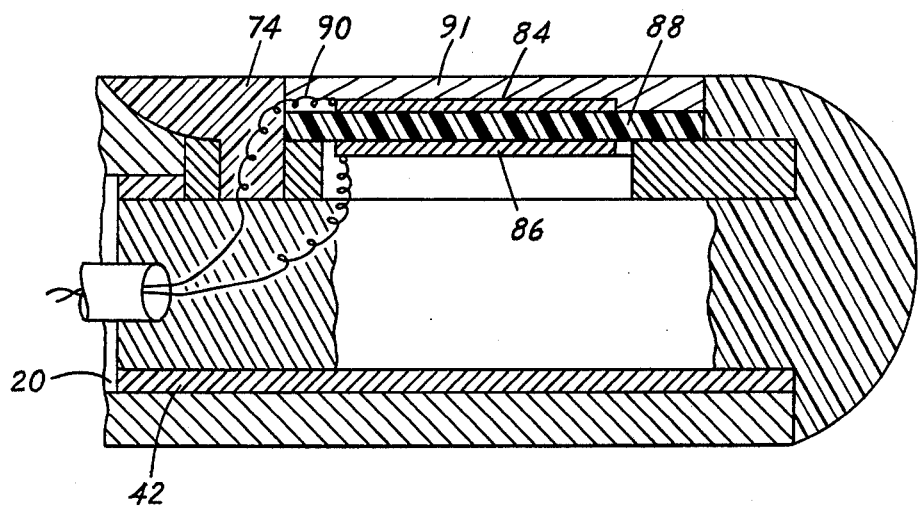
FIG. 7 is a view similar to FIG. 2 showing an alternate transducer construction.

In FIG. 7 electrodes 84 and 86 are on opposite sides of piezoelectric $PVF_2$ membrane 88, and lead 90 from electrode 84 passes through epoxy 74 to lumen 20. Insulating layer 91 covers outer electrode 84.

Figure 8:
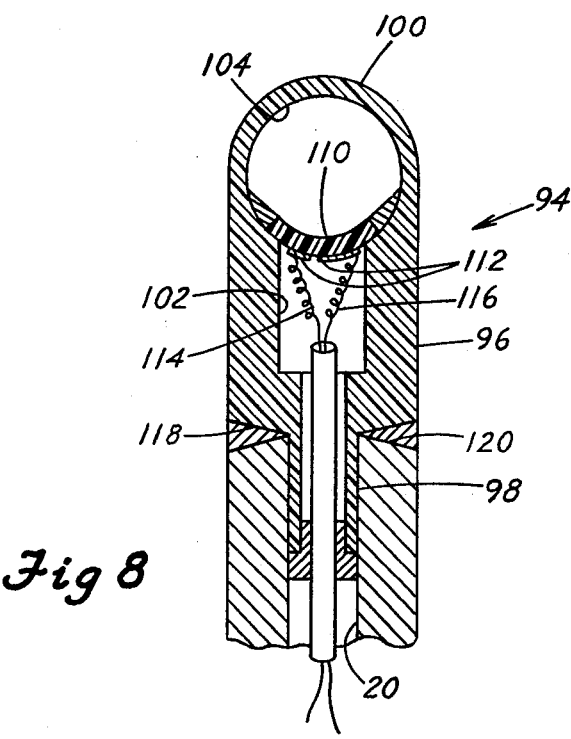
FIG. 8 is a view similar to FIG. 2 showing yet another embodiment.

In FIG. 8 stainless steel frame 94 has a main cylindrical body 96, a cylindrical portion 98 of reduced diameter that fits the end of the catheter lumen 20, and an annular tip 100. Bore 102 communicates between lumen 20 and circular opening 104 in tip 100. Circular, concave, piezoelectric membrane 110, with two electrodes 112 (e.g., in the form shown in FIG. 6) on one surface, is cemented electrodes-down to the rim of the bore 102. Leads 114 and 116 run from the electrodes through bore 102 and lumen 20. Epoxy is provided at 118 and 120. The diameter of bore 102 is large enough at its top to fully expose electrodes 112.

Figure 9:
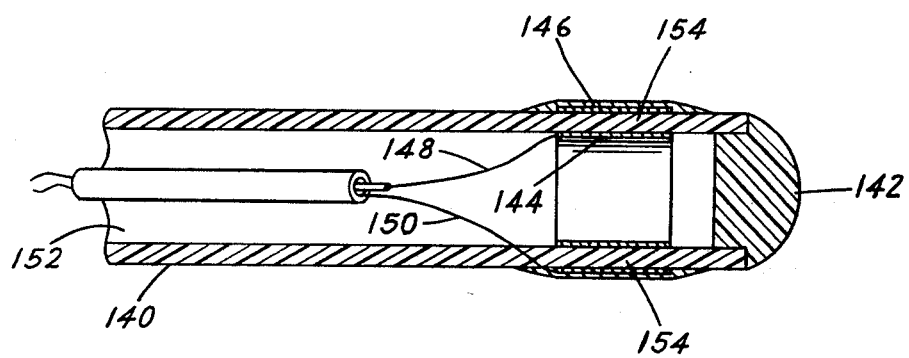
FIG. 9 is a view similar to FIG. 2 showing yet another embodiment.

In FIG. 9 the catheter tube 140 is itself of $PVF_2$, potted at its tip with epoxy 142. Electrodes 144 and 146 are concentric, 5 mm wide rings of metal deposited on the inner and outer walls of tube 140, respectively. Leads 148 and 150 run from the electrodes through lumen 152. The portion of tube 140 between the electrodes, at 154, is made piezoelectric by poling the $PVF_2$ there after application of the electrodes. Parylene insulation 160 covers outer electrode 146. A calibration lumen, as in FIG. 2, may be added.

Figure 10:
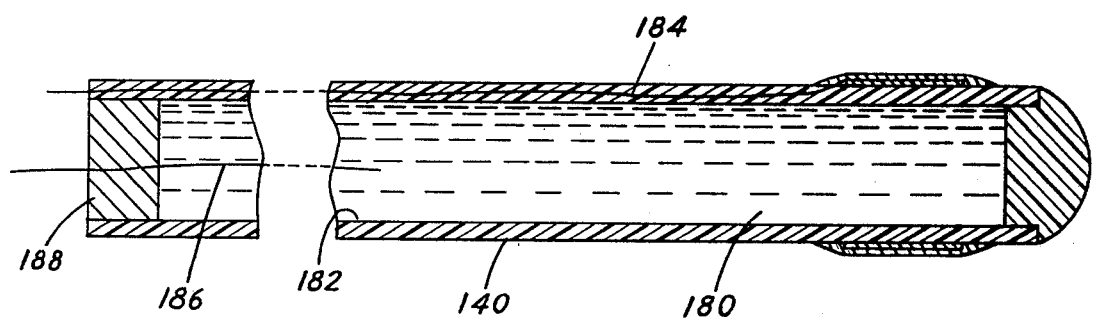
FIG. 10 is a view similar to FIG. 2 showing yet another embodiment.

In FIG. 10 the inner electrode ring 144 of FIG. 9 is replaced by electrically conductive liquid 180 sealed in lumen 182, and lead 184 is embedded in the wall of tube 140. Lead 186 is inserted directly into the liquid and exits through plug 188 at the rear of the catheter.

OPERATION

In the embodiment of FIGS. 1-6 catheter 10 is first prepared by filling lumen 26 with liquid, preferably a saline solution, and is connected to external transducer 200 through 3-way valve 202.

Catheter 10 is introduced into the desired organ where actual intraorgan pressure is measured as follows. Stress generated by pressure (in both audible and inaudible frequency ranges) in an organ acts to deform piezoelectric film 52 inwardly, thereby producing strains along its surface. Cavity 59, defined by the perimeter of opening 58 and the inner walls of stainless tube 42, is large enough to permit the unobstructed flexing of piezoelectric film 52 as it deforms inwardly, so-called "bending mode" operation. Film 52 being piezoelectric, strains therein generate an electrical charge, which is proportional to the strain, between interdigitated electrodes 54 and 56 which are attached to the surface of the film where the piezoelectric effect is very strong.

Advantageously, because transducer 50 carries electrodes on one surface only, excellent sensitivity is achieved, not only because the piezoelectric effect is strongest near the surface of film 52 where the strain is greater and where the electrodes are located, but also because electrodes 54 and 56, being on the inner surface of piezoelectric film 52, are electrically and thermally insulated by the thickness of film 52, thus avoiding electrical "noise" and various artifacts due to imperfect insulation or temperature fluctuations. The free flexing permitted by cavity 59 also enhances sensitivity. The interdigitated pattern of electrodes 54 and 56 forms relatively long and narrow evenly spaced gaps between interlocking fingers 64, 66, 68, and 70, increasing the piezoelectric effect when film 52 flexes. Further, the location of electrodes 54 and 56 on the surface of film 52, where the strain is greatest, permits use of film of increased thickness, where, for example, higher blood pressures will be encountered.

Due to the wide bandwidth of piezoelectric polymers, sound and pressure can be detected using the same sensor. The signal, transmitted through leads 60 and 62 from electrodes 54 and 56 to external circuitry (not shown), is electronically filtered, using conventional means, in two different ranges (e.g., 0-40 Hz and 50-500 Hz) and the two resulting signals are read out as pressure and sound respectively.

The rigidity of stainless steel plate 40 and stainless steel tube 42 assists in assuring proper control of the rotation and direction of the catheter tip, and avoids any undesirable artifacts due to inadvertent bending of the catheter tip by pressure acting thereon.

The mean value of intraorgan pressure is transmitted through lumen 26 (which is too long and has too large a diameter to respond with sensitivity to the detailed fluctuations in pressure measured through film 52) to transducer 200. By combining the output of transducer 200 with the outputs from leads 60 and 62, a display can be generated showing fluctuation of intraorgan pressure about its mean baseline. The baseline can be calibrated from time to time by turning valve 202 to expose transducer 200 to the atmosphere.

In the embodiment of FIG. 7, with electrodes 84 and 86 on opposite sides of membrane 88, operation is in the "bending" mode as that of the embodiments of FIGS. 1-6 but, here, in addition, the continuous electrodes on both sides of the membrane are sensitive to strain uniformly distributed throughout the thickness of the film. Insulating layer 90 thermally and electrically insulates outer electrode 84.

In the embodiment of FIG. 8 piezoelectric membrane 110 also operates in the "bending" mode. Rigid frame 94 ensures that there is no bending of piezoelectric membrane 110 other than inwardly of bore 102 which is wide enough to permit unobstructed flection of the membrane. Annular tip 100 acts as a cage to avoid dangerous contact between membrane 110 and, for example, the inner walls of blood vessels.

In the embodiments of FIGS. 9 and 10 the wall of the catheter itself beneath electrode 146 is piezoelectrically activated with the result that the inner to outer diameter ratio of tube 104 can be chosen so as to enhance sensitivity (the thinner the wall, the greater the sensitivity). The piezoelectrically activated portion of the catheter wall operates in the "bending" mode as the embodiment of FIG. 7, with parylene insulation 160 thermally and electrically insulating outer electrode 146. These embodiments offer the advantages of great simplicity in, and ease of, construction together with robustness. Moreover, reduced cost due to the ease of construction makes possible the commercial production of relatively cheap disposable catheters, there being no separate sensor. The use of a liquid electrode in FIG. 10 further simplifies construction.

Other embodiments are within the following claims.

We claim:

1. A catheter for measuring pressure fluctuations within the body, comprising
  a tube having one end suitable for insertion into a body organ,
  a transducer located at said end, said transducer comprising a flexible piezoelectric polymeric membrane having an interior surface facing the interior of said tube and an exterior surface facing the exterior of said tube, a pair of surface electrodes mounted on said membrane, said tube end having a cavity, said membrane being supported above said cavity at the periphery of the membrane so that said membrane is unsupported in the region where it overlies said cavity, and said cavity being sufficiently large to permit unobstructed inward flexing of said membrane in response to pressure fluctuations in said organ, and means for transmitting from said electrodes to external circuitry electrical signals produced by said flexing.

2. The catheter of claim 1 wherein said electrodes are both on said interior surface of said membrane.

3. The catheter of claim 2 wherein said electrodes are interdigitated.

4. The catheter of claim 1 wherein said membrane is polyvinylidine fluoride.

5. The catheter of claim 1 wherein said tube comprises a flexible plastic element and further comprising a rigid support portion located at said end supporting said membrane periphery, said rigid support portion being an insert in said tube.

6. The catheter of claim 5 wherein said insert comprises a plate member having an opening over which said membrane is mounted, said opening being part of said cavity.

7. The catheter of claim 6 wherein said tube has a lumen communicating with said opening.

8. The catheter of claim 7 wherein the entire portion of said membrane carrying said electrodes is in registry with said opening.

9. The catheter of claim 1 wherein said piezoelectric membrane is a different material than said tube.

10. The catheter of claim 9 wherein said piezoelectric membrane is made from the same material as said tube and is integral with said tube.

11. The catheter of claim 10 wherein said piezoelectric membrane is a piezoelectrically activated region of said tube near the end of said tube.

12. The catheter of claim 11 wherein said electrodes are concentric rings, one on the exterior surface of said activated region and one on the interior surface of said activated region.

13. The catheter of claim 1 wherein one said electrode is mounted on said exterior surface of said membrane and the other said electrode is mounted on said interior surface of said membrane.

14. The catheter of claim 13 wherein said electrode mounted on said exterior surface is covered with an insulating coating.

15. The catheter of claim 1 wherein said catheter further comprises means responsive to the average pressure within said organ, said averge pressure-responsive means comprising a lumen for receiving fluid to communicate between the interior of said organ and a transducer outside said organ for measuring said average pressure.

* * * * *